United States Patent [19]

Kaufmann, Jr.

[11] Patent Number: 4,664,697

[45] Date of Patent: May 12, 1987

[54] GRASS SEED HEAD SUPPRESSION PROCESS

[75] Inventor: John E. Kaufmann, Jr., Chesterfield, Mo.

[73] Assignee: Monsanto Company, St. Louis, Mo.

[21] Appl. No.: 757,395

[22] Filed: Jul. 22, 1985

Related U.S. Application Data

[63] Continuation of Ser. No. 673,448, Nov. 20, 1984, abandoned, which is a continuation of Ser. No. 519,337, Aug. 1, 1983, abandoned.

[51] Int. Cl.$^4$ .................................................. A01N 43/64
[52] U.S. Cl. .................................................. 71/92; 71/76; 71/118
[58] Field of Search ........................... 71/92, 76, 118

[56] References Cited

U.S. PATENT DOCUMENTS 3,829,306  8/1974  Ratts ..................................... 71/76
4,243,405  1/1981  Balasubramanyad et al. ......... 71/76

OTHER PUBLICATIONS

Sawyer et al., Chem. Abst. vol. 99 (1983) 100894g.
McElroy et al., Am. Soc. of Agronomy Abstracts (1983) p. 108.

*Primary Examiner*—Catherine L. Mills
*Attorney, Agent, or Firm*—Robert B. Martin; Larry R. Swaney; Frank D. Shearin

[57] ABSTRACT

Mixtures of an acetanilide derivative and a triazole derivative are found to have surprising efficacy in suppressing seed head development in turf grasses.

14 Claims, No Drawings

GRASS SEED HEAD SUPPRESSION PROCESS

This is a continuation of application Ser. No. 673,448, filed Nov. 20, 1984 now abandoned which was a continuation of Ser. No. 519,337 filed Aug. 1, 1983, now abandoned.

BACKGROUND OF THE INVENTION

This invention relates to a process for suppressing grass growth by the application of a synergestic mixture of compounds that produces an unexpectly advantageous result at low application levels.

Many compounds have been described that effectively reduce the growth of grasses. Some of these are, in fact, commercially available for this purpose. There is, however, a recurrent problem in using these compounds in that they are often so active that the margin between the level of application that produces the desired effect and the level at which the grass suffers unsightly discoloration or even death is often small. This means that there is a significant potential for damage as a result of overlapping applications or incorrect usage.

In spite of these problems, the use of compounds to suppress grass growth has expanded on roadsides and similar large area applications, and also in pasture renovation.

This suppression can take the form of an actual reduction in the amount of vegetative growth and/or in the formation of seed heads in the grass. This invention relates specifically to a method of reducing seed head formation in grass by applying thereto a synergistic mixture of two compounds that shows particular utility at low application rates.

DESCRIPTION OF THE INVENTION

The invention comprises a mixture of from 50% to 83% by weight of: (A) an acetanilide derivative having the formula:

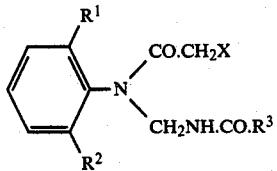

wherein $R^1$ and $R^2$ are each selected from $C_1$–$C_3$ alkyl and alkoxy groups, $R^3$ is selected from $C_1$–$C_3$ alkyl groups, and X is chloro or bromo; and from 50% to 17% by weight of: (B) a triazole derivative having the formula:

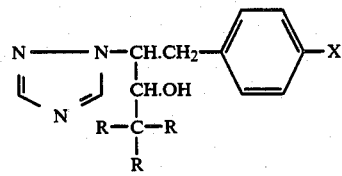

wherein R is hydrogen or methyl provided that at least one R group is methyl, and X is chloro or bromo; all percentages being based on the combined weights of A and B.

The invention further comprises a method of suppressing seed head formation in grasses which comprises applying thereto during the period commencing when the grasses are at least 50% green-up, and for about 6 weeks thereafter, but no later than the point at which seed head elongation has been initiated, an effective amount of a mixture of from 50% to 83% by weight of: (A) an acetanilide derivative having the formula:

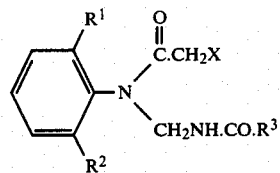

wherein $R^1$ and $R^2$ are each selected from $C_1$–$C_3$ alkyl and alkoxy groups, $R^3$ is selected from $C_1$–$C_3$ alkyl groups, and X is chloro or bromo; and (B) from 50% to 17% by weight of a triazole derivative having the formula:

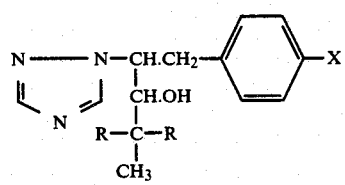

wherein each R is hydrogen or methyl and X is chloro or bromo, all percentages being based on the combined weights of A and B.

In a preferred seed head suppression method, the groups $R^1$ and $R^2$ are each ethyl and $R^3$ is methyl. The preferred X group is chloro in both components A and B of the mixture.

"Green-up" is the transition from dormancy (winter phase) to the active growth phase. "50% Green-up" is when this process is about half completed.

As regards component B of the mixture, each group R is preferably methyl.

The weight proportions of A and B are conveniently in a ratio of 5:1 to 1:1 and most preferably in a ratio of about 2:1.

The application level that is effective can vary according to the grass and the past, present, and future growing conditions.

However, it is found that the synergistic effect is diminished by an increase of the amount applied. Thus, above about 1.25 lb/acre of component A, the synergistic effect is not significant and below about 0.75 lb/acre component A does not have adequate activity alone or in combination with B. Thus, a preferred method uses up to about 1 lb/acre of component A with from 0.2 to 0.6 lb/acre of component B. Generally, an application level of below about 2 lb/acre of the combined weight ingredients A and B is preferred where cool season grasses are involved. However, with warm season grasses, higher application levels may be appropriate, perhaps as high as 3 or even 4 lbs/acre.

The mixture can be applied to the grass at any time 4 to 45 days before seed head formation would be expected in the absence of the treatment. This generally occurs about 30 days after 100% green-up and application from 5 to 20 days before seed head formation is particularly preferred.

The preparation of Component A is described for example in U.S. Pat. No. 3,829,306 and that of Component B in U.S. Pat. No. 4,205,075. Both components are known to exhibit plant growth regulating activity independently. However, the discovery that together they have an unexpectedly advantageous seed head suppressing effect on grass was very surprising, especially in view of the fact that Component B alone appears actually to enhance the formation of seed heads.

The unexpected nature of this synergistic effect is readily apparent from consideration of the following Examples which are for the purposes of illustration only and are intended to supply no essential limitation on the scope of the invention.

EXAMPLE 1

The crop tested in this Example was a large stand of Merion Kentucky bluegrass. A mixture of the compounds:

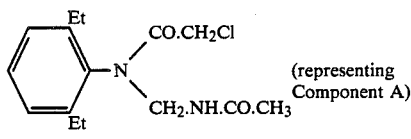
(representing Component A)

and

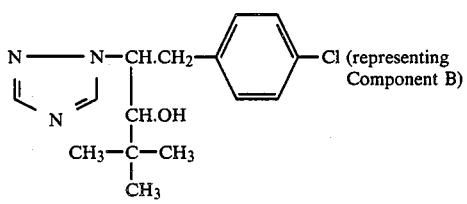
(representing Component B)

was applied at the indicated application levels to different parts of the stand. The individual components were also separately applied to provide the basis for a comparison.

Different parts of the stand were treated at different levels and for each part a nontreated control area was maintained.

The compounds were applied as an aqueous suspension using a back-pack $CO_2$ sprayer with two 11010 nozzles on a hooded boom. Where a mixture was to be applied, the components were applied sequentially back to back.

Application was on April 25 and 77 days later, the evaluation was made in the following manner. A 1 foot square frame was placed on each of three similarly treated areas. The frame was also placed on six separate control areas, one at each end of each of the three groups (replications) of the indicated application levels. The grass in each frame was carefully cut to a uniform 3 inch length and the cuttings were set aside. The number of seed heads and the weight of the cuttings in each was then determined and averaged over the three similarly treated plots and over the six control plots. The results are set forth in Table 1.

TABLE 1

|  | Control | Component A (Acetanilide) | Component B (Triazole) | Mixture (A + B) |
|---|---|---|---|---|
| Application Level (lb/A) | 0 | 1 | 0.5 | 1 + 0.5 |
| Seed Heads | 94 | 49 | 138 | 21 |
| Vegetative Growth Weight (gm/square foot plot) | 44.9 | 25.4 | 32.6 | 19.0 |
| Application Level (lb/A) | 0 | 1.5 | 0.75 | 1.5 + 0.75 |
| Seed Heads | 76 | 4 | 78 | 4 |
| Vegetative Growth Weight (gm/square foot plot) | 48.4 | 18.7 | 15.9 | 12.8 |
| Application Level (lb/A) | 0 | 2.5 | 1.5 | 2.5 + 1.5 |
| Seed Heads | 68 | 0 | 84 | 1 |

From the above, it can clearly be seen that Component B actually increases the seed head count at all application levels while Component A is an effective reducer of the count. However, at low application levels, the addition of a small amount of B to A results in a 57% reduction in seed head count. This is quite unexpected on the basis of the separate performance of that applicable level of Component B. It should be noted that this effect only becomes noticeable at levels at which Component A alone is not fully effective and that Component B therefore serves as an unexpectedly effective adjuvant for A.

EXAMPLE 2

This Example duplicates the procedures described in Example 1 except where otherwise indicated. The Kentucky bluegrass was treated on April 25, and evaluated for seed head density 52 days after treatment.

The seed head density for each square was evaluated visually on a scale of 1-9. The lowest reading indicates no visible seed heads and 9 represents complete seed head development. Once again, the readings were averaged out over the three treated plots and over the six untreated controls. The results are shown in Table 2.

TABLE 2

| Control | Component A | | Component B | | A plus B | |
|---|---|---|---|---|---|---|
| | lb/A | Density | lb/A | Density | lb/A | Density |
| 9.0 | 1.0 | 5.0 | 0.50 | 9.0 | 1 + 0.5 | 2.7 |
| 9.0 | 1.5 | 2.0 | 0.75 | 9.0 | 1.5 + 0.75 | 2.0 |
| 9.0 | 2.5 | 1.3 | 1.50 | 8.7 | 2.5 + 1.5 | 1.0 |

In addition, a vegetation height visual estimation was carried out. Again, this was on a scale of 1 to 9, with 1 equal to the original moving height of 3 inches and 9 approximately 8 inches above the original mowing height. Thus, whole number increments represent additional inches of growth.

Assessments involved no disturbance of the plots. All plants were upright and no lodging was observed. Each figure given is an average of three replications of the treated areas and six replications of the control. The details are set forth in Table 3.

TABLE 3

| Control | Component A | | Component B | | A plus B | |
|---|---|---|---|---|---|---|
| Vegetation Growth | lb/A | Vegetation Growth | lb/A | Vegetation Growth | lb/A | Vegetation Growth |
| 9.0 | 1.0 | 7.0 | 0.5 | 8.0 | 1 + 0.5 | 4.0 |
| 9.0 | 1.5 | 5.7 | 0.75 | 6.0 | 1.5 + 0.75 | 2.3 |
| 9.0 | 2.5 | 5.3 | 1.5 | 6.7 | 2.5 + 1.5 | 3.3 |

Once again, it can be seen that the advantage of the mixture only becomes apparant at levels at which Component A is not itself fully effective. In this Example, however, the synergistic effect is clearly demonstrated also in the reduction in vegetative growth.

The mixtures used in the method of this invention including concentrates which require dilution prior to application contain the active Components A and B and an adjuvant in liquid or solid form. The compositions are prepared by admixing the components with an adjuvant including diluents, extenders, carriers, and conditioning agents to provide compositions in the form of finely divided particulate solids, granules, pellets, solutions, dispersions, or emulsions. Thus, they can be used with an adjuvant such as a finely divided solid, a liquid of organic origin, water, a wetting agent, a dispersing agent, an emulsifying agent, or any suitable combination of these.

The mixtures used in the method of this invention can also be in the form of liquids and wettable powders. These preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and nonionic agents can be used with equal facility.

Preferred wetting agents are alkyl benzene and alkyl naphthalene sulfonates, sulfonated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acidesters of hexitol anhydrides (e.g., sorbitan). Preferred dispersants are methyl cellulose, polyvinyl alcohol, sodium lignin sulfonates, polymeric alkyl, nephthalene sulfonates, sodium naphthalene sulfonate, and the polymethylene bisnaphthalene sulfonate.

Wettable powders are water-dispersible compositions containing one or more active ingredients, an inert solid extender, and one or more wetting and dispersing agents. The inert solid extenders are usually of mineral origin such as the natural clays, diatomaceous earth and synthetic minerals derived from silica and the like. Examples of such extenders include kaolinites, attapulgite clay, and synthetic magnesium silicate. The wettable powder compositions of this invention usually contain from about 0.5 to 60 parts (preferably from 5 to 20 parts) of active ingredient, from about 0.25 to 25 parts (preferably 1 to 15 parts) of wetting agent, from about 0.25 to 25 parts (preferably 1.0 to 15 parts) of dispersant and from 5 to about 95 parts (preferably 5 to 50 parts) of inert solid extender, all parts being by weight of the total composition. Where required, from about 0.2 to 2.00 parts of the solid inert extender can be replaced by a corrosion inhibitor of anti-foaming agent or both.

Other formulations include concentrates comprising from 0.1 to 60% by weight of the active ingredient on a suitable extender; these dusts may be diluted for application at concentrations within the range of from about 0.1 to 10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1 to 60%, preferably 5 to 50% by weight, of active ingredient, the upper limit being determined by the solubility limit of active ingredients in the solvent.

In another form of aqueous suspensions, a water-immiscible component is encapsulated to form microencapsulated phase dispersed in an aqueous phase. In one embodiment, minute capsulates are formed by bringing together an aqueous phase containing a lignin sulfonate emulsifier and a water-emmiscible chemical and polymetnylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l. The microencapsulation process referred to here is described in more detail in U.S. Pat. No. 4,280,833.

Concentrates are usually solutions of the active ingredients in water-immiscible or partially water-immiscible solvents together with a surface active agent. Suitable solvents for the active ingredients of this invention include dimethylformide, dimethylsulfoxide, N-methylpyrrolidone, hydrocarbons, and water-immiscible ethers, esters or ketones. However, other high strength liquid concentrates may be formulated by dissolving the active ingredient in a solvent then diluting, e.g., with kerosene, to spray concentration.

The concentration compositions herein generally contain from about 0.1 to 95 parts (preferably 5 to 60 parts) active ingredient about 0.25 to 50 parts (preferably 1 to 25 parts) surface active agent, and where required, about 4 to 94 parts solvent, all parts being by weight based on the total weight of emulsifiable oil.

Granules ae physically stable particulate compositions comprising the active ingredients adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, gypsum, and vermiculite are examples of operable classes of particulate mineral extenders. The preferred extenders are the porous, absorptive, preformed particles such as performed and screened particulate attapugite or heat expanded, particulate vermiculite and the finely-divided clays such as kaolin clays, hydrated attapulgite, or bentonitic clays. These extenders are sprayed or blended with the active ingredient to form the herbicidal granules.

Granular compositions useful in this invention may contain from about 0.1 to about 30 parts, preferably from about 0.5 to 10 parts by weight of active ingredient per 100 parts by weight of clay and 0 to about 5 parts by weight of surface active agent per 100 parts by weight of particulate clay.

Components A and B can also be added together with other additaments; for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid, or phenol derivatives, thiolcarbamates, triazoles, benzoic acids, nitriles, biphenyl ethers and the like.

Fertilizers useful in combination with the active ingredients include, for example, ammonium nitrate, urea, potash, and superphosphate. Other useful additaments include materials in which plant organisms take root and grow such as compost, manure, humus, sand, and the like.

What is claimed is:

1. A composition useful for grass seedhead suppression comprising a mixture of a major portion to 83% by weight of:

A. an acetanilide having the formula:

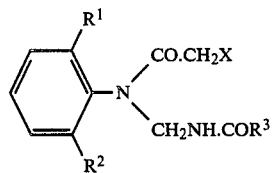

wherein $R^1$ and $R^2$ are each selected from $C_1$–$C_3$ alkyl and alkoxy groups, $R^3$ is selected from $C_1$–$C_3$ alkyl groups, and X is chloro or bromo; and at least 17% by weight of:

B. a triazole derivative having the formula:

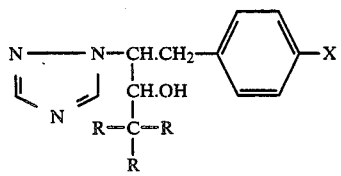

wherein each R is hydrogen or methyl and X is chloro or bromo, all percentages being based on the combined weights of A and B.

2. A composition according to claim 1 in which, in A, $R^1$ and $R^2$ are both ethyl and $R^3$ is methyl.

3. A composition according to claim 1 in which, in B, both groups R are methyl.

4. A composition according to claim 1 in which, in both A and B, X is chloro.

5. A composition according to claim 1 in which A and B are present in a ratio of from 5:1 to 2:1.

6. A composition useful for grass seed head suppression comprising about two parts by weight of an acetanilide having the formula:

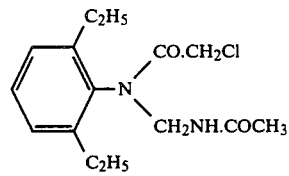

and about one part by weight of a triazole having the formula:

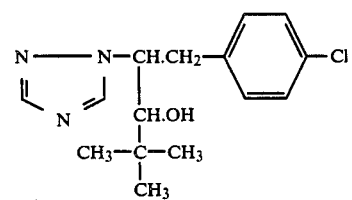

7. A method of suppressing seed head formation in grasses which comprises applying to the grasses during the period commencing when the grasses are at least 50% green-up, and for about six weeks thereafter, but no later than the point at which seed head elongation has been initiated, an effective amount of a mixture at application levels such that about 0.75 to 1.25 lb/acre of component A and about 0.2 to 0.6 lb/acre of component B are applied of a composition according to claim 1.

8. A method according to claim 7 in which the mixture is applied at such a rate that about 1 lb/acre of A is applied.

9. A method according to claim 7 in which the grass is treated up to 45 days before normal seed head formation.

10. A method according to claim 7 in which the composition is as specified in claim 2.

11. A method according to claim 7 in which the composition is as specified in claim 3.

12. A method according to claim 1 in which the composition is as specified in claim 4.

13. A method according to claim 7 in which the composition is as specified in claim 5.

14. A method of suppressing seed head formation in grasses which comprises applying to the grasses up to 45 days before normal seed head formation a mixture comprising:

A. A compound having the formula:

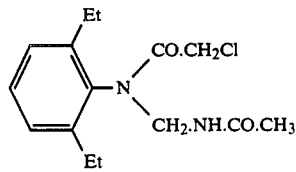

and

B. A compound having the formula:

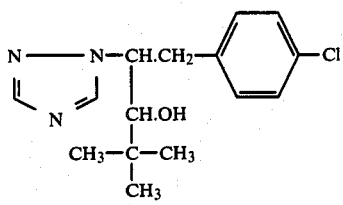
at application levels such that from 0.75 to 1.25 lb/acre of A and from 0.2 to 0.6 lb/acre of B are applied.
* * * * *
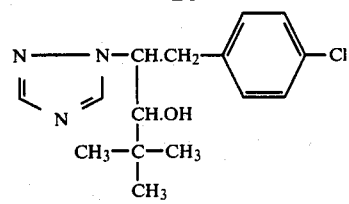
at application levels such that from 0.75 to 1.25 lb/acre of A and from 0.2 to 0.6 lb/acre of B are applied.
* * * * *